United States Patent [19]
Weatherford et al.

[11] Patent Number: 5,718,243
[45] Date of Patent: Feb. 17, 1998

[54] PALATE PROTECTIVE DEVICE

[76] Inventors: Shirley Weatherford, 13520 Mt. Castle, Dallas, Tex. 75234; Dona Taylor, 2917 Cambridgeshire, Carrollton, Tex. 75007; Chrysty Graves, 2309 Dana Dr., Rowlett, Tex. 75088

[21] Appl. No.: 662,218

[22] Filed: Jun. 12, 1996

[51] Int. Cl.[6] .................................................. A61C 5/14
[52] U.S. Cl. ........................................ 128/859; 128/861
[58] Field of Search .................................. 128/859–862; 2/2

[56] References Cited

U.S. PATENT DOCUMENTS

| | | | |
|---|---|---|---|
| 2,669,988 | 2/1954 | Carpenter | 128/861 |
| 3,126,002 | 3/1964 | Owens | 128/861 |
| 4,270,531 | 6/1981 | Blachly | 128/861 |
| 5,031,638 | 7/1991 | Castaldi | 128/861 |
| 5,195,513 | 3/1993 | Sinko et al. | |
| 5,533,523 | 7/1996 | Bass | 128/859 |

OTHER PUBLICATIONS

*Gesco Pla–Nate*™ *Palate Guard* Brochure, GESCO International, Inc., a subsidiary of MedChem Products, Inc., Mar. 1993.

Primary Examiner—Michael A. Brown
Attorney, Agent, or Firm—Jenkens & Gilchrist; J. Kevin Gray

[57] ABSTRACT

An improved palate protector for infants and neonates is disclosed. The highly flexible and deformable main body of the palate protector is positioned within the mouth of an infant or neonate between the palatal surface and a orotracheal tube to protect the palatal area, upper inside gum and frenulum of the infant from injury and malformation resulting from the use of the orotracheal tube. A groove in the forward arcuate edge of the main body of the palate protector prevents irritation and injury of the frenulum of the infant. An elongated, highly flexible and tapered front tab projecting from the main body of the palate protector is used to removably secure the orotracheal tube to the palate protector and to the infant or neonate.

5 Claims, 4 Drawing Sheets

PALATE PROTECTIVE DEVICE

TECHNICAL FIELD

The present invention relates to palate protective devices, and more specifically, to an improved palate protective device for neonates requiring orotracheal intubation.

BACKGROUND OF THE INVENTION

Neonates and certain infants often require prolonged orotracheal intubation to combat various conditions and illnesses. For example, low birth weight neonates may require such prolonged intubation to combat respiratory distress. Moreover, orotracheal intubation has been identified as causing certain malformations of the palate, such as palatal grooving. Indeed, it has been shown that such malformations can occur within the first twelve hours of orotracheal intubation. Such malformations result from the constant pressure and movement applied to the palate by orotracheal tubes.

Immature infants and neonates are particularly susceptible to such malformations due to a weakened palatal configuration. Additionally, malformations of the palate can become permanent, resulting in future problems with speech, feeding, hearing and future dental and orofacial development.

Accordingly, several prior art devices have been developed to protect against the above-identified malformations. Traditional approaches to this problem include bite blocks" and customized palate guards. As the name suggests, bite blocks require an individual to position a block of rigid material between the upper and lower teeth to secure the orotracheal tubes and prevent the adverse side effects created by such tubes. While this type of device has enjoyed a modicum of success when used in adults, the device has obvious limitations with respect to infants and neonates since such individuals lack formed teeth.

Customized palate guards have also been developed to protect the palates of infants and neonates. Examples of such devices are described in Fadavi, S, et al., *Use of a Palatal Stabilizing Device in prevention of Palatal Grooves in Premature Infants*, CRITICAL CARE MEDICINE 18: 1279–81, 1990. Using such a device, a maxillary impression of the palate to be protected is taken and a cast prepared. From the cast, a palate guard is produced to snugly fit the palate to be protected. Due to the custom fit of the palate guard, however, such guards are expensive and difficult to make for extremely small infants and neonates. Additionally, the guards must be cleaned daily and a new guard produced every few weeks as the neonate grows and the size and shape of the palate changes, thus adding to the expense and intrusion of care. Finally, since the guard is substantially rigid, the soft tissue of the palate is at risk of being damaged by use of such a guard.

Recently, a less-customized palate prothesis has been developed for protection of infant and neonatal palates. Such a prothesis is described in U.S. Pat. No. 5,195,513 to Sinko et al. This type of palate prothesis is a mass of deformable plastic which is placed between the palate tissue of the infant or neonate and the orotracheal tube. While this device avoids some of the problems associated with other prior art devices, unfortunately, in practice, this type of prothesis has been shown to be relatively ineffective for a variety of reasons.

Although somewhat deformable, the prior art prothesis remains substantially rigid, thus exposing the soft tissue of the palate to damage. The relatively bulky nature of the "mass" of the prothesis also renders it difficult to place, secure and use within the relatively small palatal area of an infant or neonate. Additionally, this type of prior art prothesis includes a continuous upstanding lip around the alveolar edge which has the potential to irritate, cut and otherwise injure the frenulum of a neonate or infant during use. Moreover, the design of the prothesis makes the device difficult to position and secure. Finally, the relatively short, stubby and inflexible nature of the frontal tab prevents the prothesis from being properly secured in the mouth, exposing the infant and neonate to the potential for the prothesis to slip backwards and block the airway of the infant.

Thus a need remains for a palate protector for infants and neonates which protects the palate from palatal malformations as a result of prolonged use of orotracheal tubes also having the flexibility, deformability and design necessary to allow such protector to be effectively and conveniently used in a clinical setting.

SUMMARY OF THE INVENTION

The improved palate protector of the present invention overcomes the foregoing and other problems associated with the prior art by providing a palate protector comprised of a relatively thin, highly flexible main body portion and a relatively long, narrow and thin front tab used to secure the palate protector in place. The main body and front tab of the palate protector includes an integral, downwardly opening channel which guides the orotracheal tube and a grooved alveolar forward edge, which protects the frenulum of the infant from irritation and injury.

Importantly, the improved palate protector of the present invention is composed of a medical grade, biocompatible material which is generally shape-retaining but highly flexible and deformable. These and other features of the improved palate protector provide an infant requiring orotracheal intubation with effective, inexpensive and non-customized palatal protection. As used herein, the term "infant" includes neonates and infants of all ages and the term "orotracheal tube" encompasses endotracheal tubes required to be maintained in the mouth and throat of an infant or neonate.

The improved palate protector of the present invention comprises a main body composed of a biocompatible, highly flexible material and a frontal tab. The main body portion of the improved palate protector shields the palate of an infant from palate malformation produced by orotracheal tubes by physically separating the orotracheal tube from the palate surface. The main body portion includes an integral, downwardly opening channel which receives and guides the orotracheal tube. The alveolar (forward) edge of the main body portion includes a groove which is shaped and positioned to protect the frenulum of the infant from irritation or injury by the palate protector during its use.

The front tab portion of the palate protector located on the forward surface of the main body and underneath the frenulum groove is relatively long, slender and highly flexible. This tab facilitates the proper placement and securement of the palate protector in use. The tab is used as an anchor for taping or otherwise securing the palate protector in place.

Although not fully-customized, thus avoiding the cost and interruption of care associated with such devices, the improved palate protector of the present invention is available in several sizes. Due to its relatively generic nature and high degree of flexibility, a particular size will fit a range of sizes and shapes of palates of infants.

In use, the first step is the selection of the appropriate size of the improved palate protector for the infant. Once the infant is intubated, the main body portion of the palate protector is placed in the mouth, the upper surface substantially corresponding to the surface of the palate and the orotracheal tube received by and guided along the downwardly opening channel. When properly placed, the frontal tab extends out of the mouth of the infant and lies flat along the orotracheal tube. The orotracheal tube is removably secured to the front tab with surgical tape or the like. The relatively long and slender nature of the front tab provides the substrate needed to efficiently and effectively secure the palate protector to the orotracheal tube and the infant. This type of securement maintains the proper position of the palate protector and prevents the protector from slipping backwards and blocking the airway of the infant. As needed, the orotracheal tube is detached from and reattached to the front tab of the palate protector.

In one embodiment of the improved palate protector of the present invention, the protector is comprised of a substantially clear, transparent or translucent material. The relative clarity of the material enhances the proper placement of the protector in the mouth of the infant as well as the proper placement of the orotracheal tubes in the downwardly opening channel of the main body.

In a different embodiment of the improved palate protector of the present invention, the substantially transparent or translucent material of the protector is tinted with color. The faint color does not obscure the clarity of the material but provides a visual contrast to the mouth, gum and palatal area of the infant.

BRIEF DESCRIPTION OF THE DRAWINGS

For a more complete understanding of the present invention and the advantages thereof, reference is now made to the following description taken in conjunction with the accompanying drawings in which.

DETAILED DESCRIPTION OF THE DRAWINGS

Figure 1:
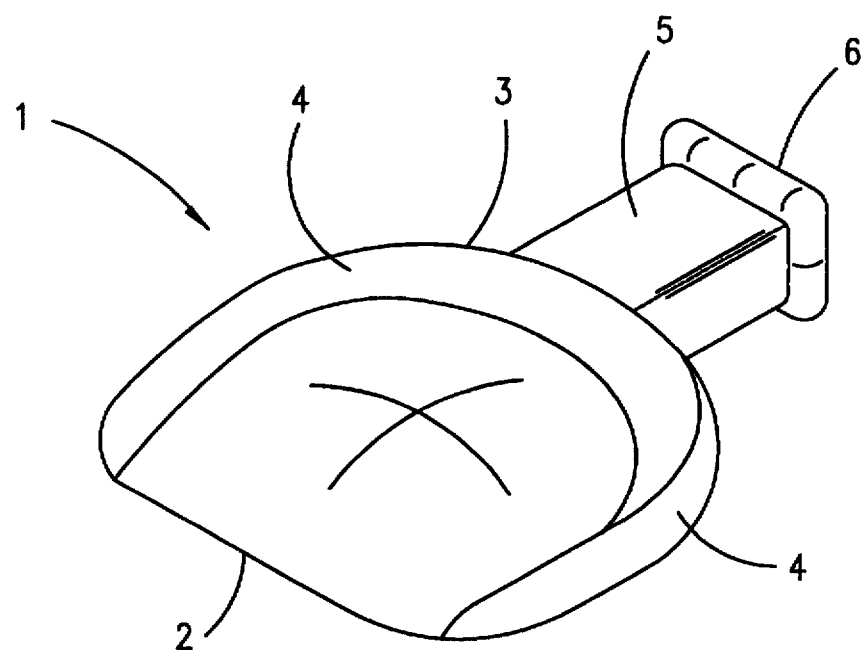
FIG. 1 is a perspective view of a prior art palate protection device.

Referring to FIG. 1, there is shown a perspective view of a prior art palate protection device lacking many of the key features of the improved palate protector of the present invention. The prior art protector 1 is comprised of a relatively thick and inflexible main portion 2 having a curved shaped front edge 3, a continuous, upstanding lip 4 of the front edge 3 and a relatively short, thick, inflexible stem 5 attached to the front of the main portion 2. The stem 5 includes a raised ridge 6 at its tip. The lower surface of the main portion 2 includes an arch 7 which approximates the palatal arch of an infant.

Although the prior art protector 1 is composed of a deformable material, its bulky construction renders the device relatively inflexible, making positioning for fit and use of the prior art device difficult. Additionally, this relatively bulky and inflexible nature prevents the protector 1 from being utilized on a range of sizes of palatal areas. Finally, the relative inflexibility of the main portion 2 actually subjects the palatal area to be protected to injury.

The continuous, upstanding lip 4 of the front edge 3 has the potential to irritate and cause injury to the frenulum and upper gum area of an infant during use. The frenulum is at risk of irritation and ultimate injury from forces exerted by the continuous, upstanding lip 4 on the area. Specifically, as the orotracheal tube and the protector 1 inevitably move and shift, the lip 4 cuts into the soft tissue of the frenulum and surrounding area.

Perhaps the largest disadvantage of the prior art protector 1 is the relatively short, thick and inflexible stem 5. It has been found that the stem 5 is too short and inflexible to be properly manipulated during use to secure the orotracheal tube thereto and to the infant. Additionally, the relatively short nature of the stem 5, coupled with the inclusion of a raised ridge 6 at its tip, prevents the stem 5 from being folded back on itself to further secure the protector 1 to the orotracheal tube and the infant.

Figure 2:
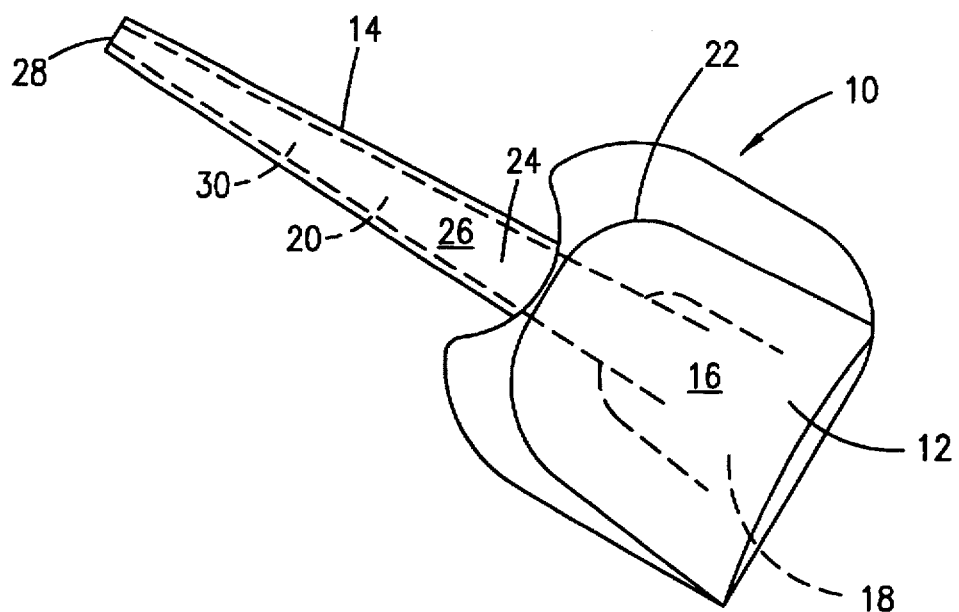
FIG. 2 is a perspective view of one embodiment of the improved palate protector of the present invention.
Figure 3:
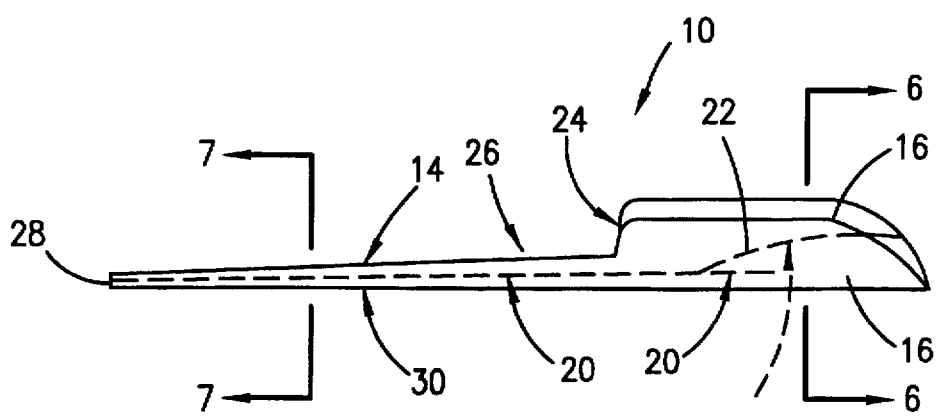
FIG. 3 is a side view of one embodiment of the improved palate protector of the present invention illustrated in FIG. 2.

Referring now to FIGS. 2 and 3, in which like elements are designated by like reference numerals, there is shown an embodiment of the improved palate protector of the present invention. In one preferred embodiment, the palate protector 10 comprises a main body 12 and a front tab 14. The main body 12 includes an upper surface 16 arched to substantially conform to the palatal surface of an infant, a lower surface 18 including a corresponding, but less pronounced, arch, and an integral downwardly opening channel 20 within the lower surface 18. The main body 12 also includes an arcuate alveolar edge 22 which is shaped to substantially conform to the upper gum of an infant. Importantly, the arcuate alveolar edge 22 includes a groove 24 at its middle. When in use, the frenulum of the infant rests within the groove 24, protecting the frenulum from irritation or injury from the palate protector 10. Irritation and/or injury to the frenulum is a major drawback associated with prior art palate protection devices such as that illustrated in FIG. 1.

The front tab 14 of the palate protector 10 is elongated, slender, smooth and highly flexible, having a first end 26 and a tapered tip 28. The front tab 14 tapers along its length such that the tapered tip 28 of the front tab 14 is more flexible than the first end 26. These features of the palate protector 10 have been found to be crucial to the proper securement of the palate protector 10 within the mouth of an infant. It has been found that prior art palate protheses are difficult to easily, quickly and effectively secure into proper position due to the relatively short, thick and inflexible nature of this feature (See FIG. 1).

Figure 4:
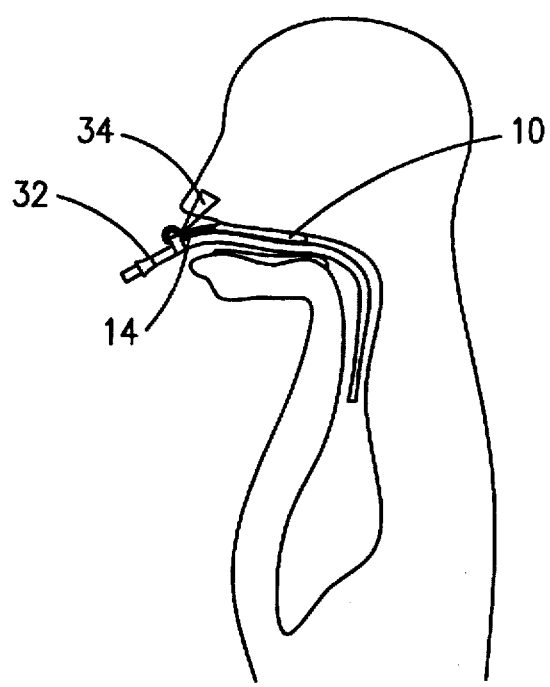
FIG. 4 is a side view of an infant, illustrating placement and securement of improved palate protector of the present invention.
Figure 5:
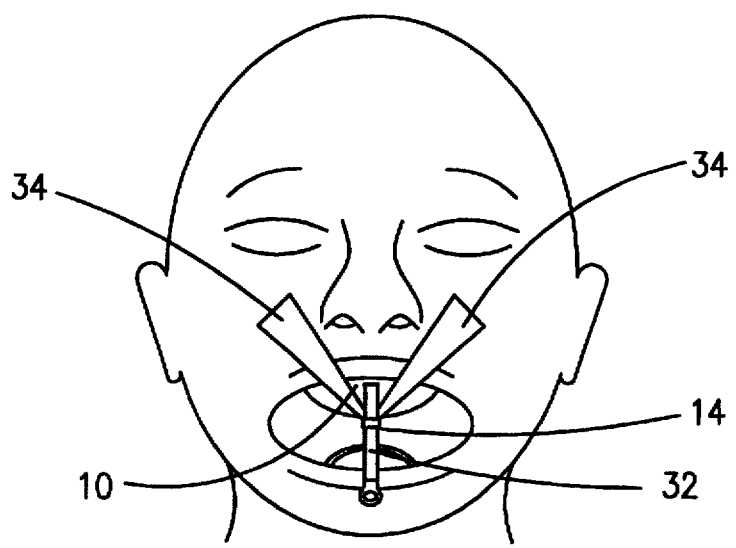
FIG. 5 is a front view of an infant, illustrating placement and securement of improved palate protector of the present invention.

The development of the unique front tab 14 of the palate protector 10 has provided a remedy to such traditional problems. As illustrated in FIGS. 4 and 5, since the front tab 14 is elongated, smooth and slender, the front tab 14 is easily manipulated when the orotracheal tube 32 is being attached to it and to the infant. Additionally, again due to its relative length, flexibility and taper, it is easily folded back unto itself to assist with attaching the orotracheal tube 32 to the front tab 14 and securing the same to the infant. It has been discovered that it is crucial that the front tab 14 be of sufficient length and flexibility to allow the orotracheal tube 32 to be removably attached to the front tab 14 utilizing surgical tape 34 or the like. It also has been discovered that the length of front tab 14 be preferably at least equal to the length of the main body 12 of the palate protector 10 to allow the front tab 14 to fold back onto itself to prevent slippage of the palate protector. In clinical tests, the unique features of the front tab 14 has been shown to be a key element in the quick, efficient and effective use of the palate protector 10.

The downwardly opening channel 20 of the main body 12 is continued along the lower surface 30 of the front tab 14. In use, the orotracheal tube 32 (illustrated in FIGS. 4 and 5) is received by the channel 20, thus providing a guide for the path of the tube through the infant's mouth and providing the physical separation of the orotracheal tube and the infant's palatal surface.

Figure 6:
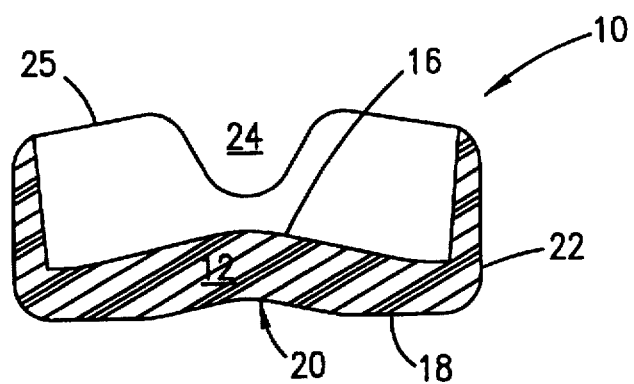
FIG. 6 is a cross section of the main body of the improved palate protector of the present invention.
Figure 7:
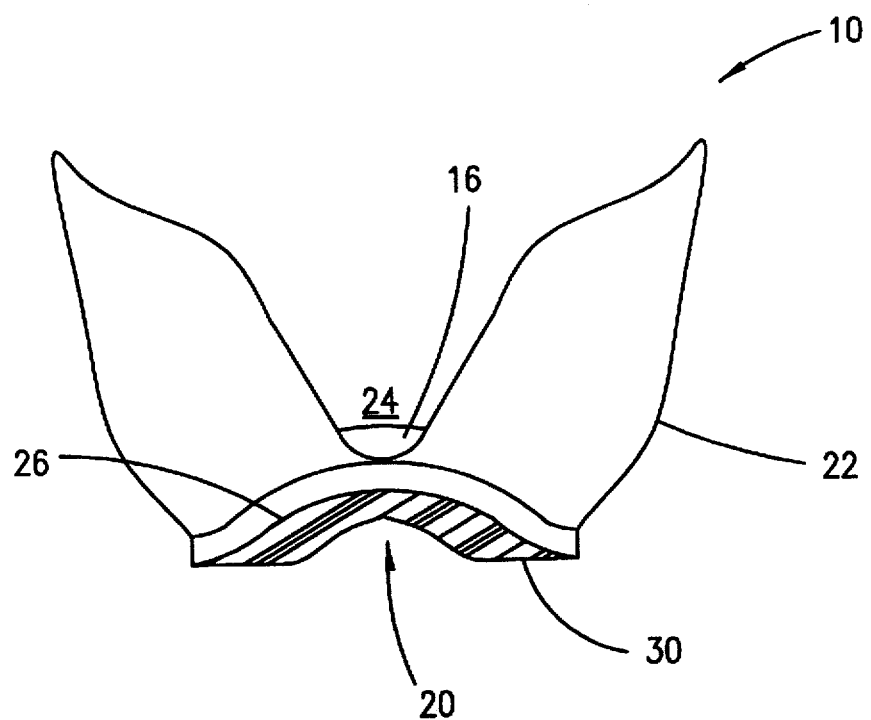
FIG. 7 is a cross section of tab of the improved palate protector of the present invention.

As illustrated in FIG. 6, the downwardly opening channel 20 is broadened within the lower surface 18 of the main body 12 of the improved palate protective device 10 when compared with the downwardly opening channel 20 within the lower surface 30 of the front tab 14 (FIG. 7). The upper surface 16 of the main body 12 is arched to substantially conform to the palatal surface of an infant during use. Also illustrated in FIG. 6 is the raised portion 25 of the arcuate alveolar edge 22. In FIG. 7, the downwardly opening channel 20 within the lower surface 30 of the front tab 14 is narrower than the downwardly opening channel 20 in the lower surface 18 of the main body 12. Also illustrated is the groove 24 of the arcuate alveolar edge 22.

In a preferred embodiment, the palate protector is comprised of a highly flexible, biocompatible material, such as silicone, which is transparent or translucent in nature. One example of an appropriate silicone material is Silastic® biomedical silicone from Dow Corning. The relative clarity of the material aids visually with the placement, securement and use of the palate protector 10. Alternatively, the material can be tinted with color. The faint color will not obscure the visual advantage gained by the relative clarity of the material, but will provide a visual contrast to aid visual inspection of the palate protector 10.

An important characteristic of the improved palate protector 10 is that the main body 12 of the palate protector 10 is highly deformable but generally shape-retaining. While some prior art palate protective devices are generally soft and deformable in nature, clinical testing has shown that they lack the high degree of flexibility and deformability needed to provide a comfortable and effective fit along the palatal area of an infant. The relatively high degree of flexibility and shape-retaining deformability of the improved palate protector 10 provides such a fit and also allows each size of the palate protector 10 to fit a range of sizes and shapes of palatal areas. The front tab 14 is comprised of the same highly flexible, highly deformable but generally shape-retaining material but exhibits an even higher degree of flexibility due to its slender, narrow and tapered nature. It is noted that although the palate protector 10 is preferentially injection molded as a single piece, the palate protector 10 can be manufactured in any other suitable manner as a single unit or as a main body and front tab portion formed separately and then joined by any suitable method, if desired.

Although preferred embodiments of the invention have been illustrated in the accompanying drawings and described in the foregoing Detailed Description, it will be understood that the invention is not limited to the embodiments disclosed, but is capable of numerous rearrangements and modifications of parts and elements without departing from the spirit of the invention.

We claim:

1. An improved palate protector for protecting the palatal surface, upper inside gum and frenulum of an infant from injury and malformation from the placement and prolonged use of an orotracheal tube, comprising:

a main body having an upper surface and a lower surface;

said upper surface including an arcuate forward edge approximating the shape of the upper inside gum of the infant;

said arcuate forward edge including a raised portion along its periphery;

said raised portion having a groove therein to protect the frenulum of the upper inside gum of the infant;

said upper surface having a generally arched shape substantially conforming to the palatal surface of the infant;

said lower surface having a generally arched shape less pronounced than the arched shape of the upper surface and including a downwardly opening channel extending substantially the entire length of the main body to receive the orotracheal tube;

an elongated front tab extending from the forward edge of the main body, having a first end and a tip;

said front tab extending in length at least equal to the length of the main body and being of sufficient flexibility to allow the front tab to be folded back onto itself, said elongated front tab tapering along its length from the first end to the tip and having an upper surface and a lower surface;

said lower surface of the elongated front tab including a downwardly opening channel extending substantially the entire length of the front tab and corresponding to the downwardly opening channel of the main body to receive the orotracheal tube;

said main body positioned between the palatal surface of the infant and the orotracheal tube so as to protect the palatal surface of the infant from injury and malformation from prolonged use of the orotracheal tube.

2. The palate protector of claim 1, wherein the main body and front tab are constructed of a medical grade, biocompatible, shape-retaining material having a high degree of flexibility and deformability.

3. The palate protector of claim 2, wherein the material is transparent or translucent in nature.

4. The palate protector of claim 3, wherein the material is colored to provide visual contrast to the palatal area of the infant.

5. The palate protector of claim 1, wherein the elongated front tab is at least equal in length to the length of the main body.

* * * * *